(12) United States Patent
McArdle et al.

(10) Patent No.: US 8,647,334 B2
(45) Date of Patent: Feb. 11, 2014

(54) APPARATUS AND PROCESSES FOR PREVENTING OR DELAYING ONE OR MORE SYMPTOMS OF PRESBYOPIA

(75) Inventors: George J. McArdle, Naperville, IL (US); Brian L. Olejniczak, Pleasanton, CA (US); Jerry R. Kuszak, Chicago, IL (US)

(73) Assignee: Lenticular Research Group LLC, Naperville, IL (US)

( * ) Notice: Subject to any disclaimer, the term of this patent is extended or adjusted under 35 U.S.C. 154(b) by 0 days.

(21) Appl. No.: 12/939,034

(22) Filed: Nov. 3, 2010

(65) Prior Publication Data
US 2011/0160709 A1 Jun. 30, 2011

Related U.S. Application Data

(60) Continuation of application No. 11/811,688, filed on Jun. 12, 2007, now abandoned, which is a division of application No. 10/980,700, filed on Nov. 2, 2004, now Pat. No. 7,252,662.

(51) Int. Cl.
*A61B 18/20* (2006.01)
(52) U.S. Cl.
USPC .......................... 606/6; 606/4; 606/5; 606/10
(58) Field of Classification Search
USPC ............... 607/88, 89; 351/205–212; 606/3–6, 606/10–12, 16–19
See application file for complete search history.

(56) References Cited

U.S. PATENT DOCUMENTS

| | | | | |
|---|---|---|---|---|
| 4,744,360 A * | 5/1988 | Bath | | 606/6 |
| 4,950,266 A * | 8/1990 | Sinofsky | | 606/2 |
| 5,599,340 A * | 2/1997 | Simon et al. | | 606/4 |
| 6,497,701 B2 * | 12/2002 | Shimmick et al. | | 606/5 |
| 6,585,723 B1 * | 7/2003 | Sumiya | | 606/5 |
| 7,146,983 B1 * | 12/2006 | Hohla et al. | | 128/898 |
| 7,278,990 B2 * | 10/2007 | Gwon | | 606/5 |
| 2002/0004658 A1 * | 1/2002 | Munnerlyn et al. | | 606/5 |
| 2002/0099363 A1 * | 7/2002 | Woodward et al. | | 606/5 |
| 2003/0023231 A1 * | 1/2003 | Bille | | 606/5 |
| 2003/0229339 A1 * | 12/2003 | Bille | | 606/5 |
| 2004/0199149 A1 | 10/2004 | Myers et al. | | |
| 2010/0114079 A1 * | 5/2010 | Myers et al. | | 606/5 |

OTHER PUBLICATIONS

Japanese Official Action issued Jan. 24, 2011 in Japanese Application No. 2007-539324.

* cited by examiner

*Primary Examiner* — Ahmed Farah
(74) *Attorney, Agent, or Firm* — Neal, Gerber & Eisenberg LLP

(57) ABSTRACT

The present invention generally relates to an apparatus and processes for preventing or delaying presbyopia. More particularly, the present invention relates to processes and apparatus for ablating epithelial cells in the germinative zone or the pregerminative zone of the crystalline lens of the eye so that onset or progression of presbyopia or one or more symptoms is delayed or prevented.

19 Claims, 8 Drawing Sheets

APPARATUS AND PROCESSES FOR PREVENTING OR DELAYING ONE OR MORE SYMPTOMS OF PRESBYOPIA

CROSS-REFERENCE TO RELATED APPLICATIONS

This application is a continuation of U.S. application Ser. No. 11/811,688, filed Jun. 12, 2007, abandoned, which is a division of U.S. application Ser. No. 10/980,700, filed Nov. 2, 2004, now U.S. Pat. No. 7,252,662, which are incorporated by reference herein.

FIELD OF THE INVENTION

The present invention generally relates to an apparatus and processes for preventing or delaying presbyopia. More particularly, the present invention relates to processes and apparatus for ablating epithelial cells in the germinative zone or the pregerminative zone of the crystalline lens of the eye so that onset or progression of presbyopia or one or more symptoms is delayed or prevented.

BACKGROUND OF THE INVENTION

Presbyopia is the impairment of vision due to advancing years or old age. Presbyopia is what causes a middle-aged or older person to hold a newspaper, magazine, or book at arm's length to read it. Many presbyopic individuals wear bifocals to help them cope with presbyopia. Presbyopia is typically observed in individuals over 40 years of age. Presbyopic individuals suffering from presbyopia may have normal vision, but the ability to focus on near objects is at least partially lost over time, and those individuals come to need glasses for tasks requiring near vision, such as reading. Presbyopia affects almost all individuals over the age of 40 to a greater or lesser degree.

For an eye to produce a clear image of objects at different distances, the effective focal length of the eye is adjusted to keep the image of the object focused on the retina at the back of the eye. Accommodation refers to this change in effective focal length. Accommodation is the ability of the eye to change its focus and is accomplished primarily by varying the shape of the crystalline lens. Accommodation provides the ability to change focus from distant objects to near objects. The ability to change focus from distant objects to near objects is impacted by presbyopia.

The shape of the crystalline lens is varied by the use of certain muscles and structures within the eye. As shown in FIG. 1, the crystalline lens 114 is located in the forward part of the eye. The crystalline lens has a generally circular cross-section having two convex refracting surfaces. The curvature of the posterior surface of the lens (which is nearer to the vitreous body) is greater than that of the anterior surface. The crystalline lens is suspended by a circular assembly of collagenous fibers called zonules 104, which are attached at their inner ends to the lens capsule (the outer surface of the crystalline lens) and at their outer ends to the ciliary body 115, a muscular ring of tissue located just within the outer supporting structure of the eye, the sclera 101. The ciliary body 115 is relaxed in the unaccommodated eye and therefore assumes its largest diameter.

During an individual's life, the crystalline lens continues to grow by epithelial cell division at the equator of the crystalline lens and formation of differentiated fiber cells from some epithelial cells. Presbyopia is believed to occur at least partially because of continued growth of the crystalline lens. One result of such growth is a progressive reduction in the flexibility of the crystalline lens, thus leading to the continuous decrease of accommodation. The growth in size of the lens in the confines of the capsule cause it to lose its ability to focus.

Previous approaches to treating presbyopia have been addressed to the cornea or sclera of the eye, although there have been suggestions to treat presbyopia by addressing the crystalline lens. According to http://www.allaboutvision.com/visionsurgery/presbyopia_surgery_2.htm, while some surgeons work with the sclera, others think the lens might be the key to presbyopia surgery, and they have proposed two techniques but have not yet begun experiments. One technique, called photophako reduction (PPR), would employ a laser to create cavities in the lens, thereby reducing its size. Another technique, called photophako modulation (PPM) would employ a laser to create minute perforations in the lens to soften it. Another technique involves using a photodisruptive laser to soften the inside of the crystalline lens to restore elasticity.

Other attempts to treat presbyopia have involved addressing the sclera or zonules. Laser Presbyopia Reversal (LAPR) involves using infrared lasers for ablation of parts of the sclera. Surgeons use the lasers to make spoke-like excisions in the sclera to thin it and give the lens more room to function. Another approach called Anterior Ciliary Sclerotomy (ACS) has attempted to make the fibers attached to the lens taut by placing several partial thickness incisions on the sclera or white part of the eye in a radial pattern. Some surgeons have placed silicone implants inside the radial incisions, trying to prevent the regression. Yet another technique for tightening the lens fibers involves applying an infrared laser to strategically thin the sclera.

U.S. Pat. No. 5,465,737 (Schachar) and other patents issued to the same inventor describe treating presbyopia and hyperopia by a method which increases the amplitude of accommodation by increasing the effective working distance of the ciliary muscle in the presbyopic eye. Schachar states that presbyopia is also arrested by inhibiting the continued growth of the crystalline lens by application of heat, radiation or antimitotic drugs to the epithelium of the lens.

Other techniques for treating presbyopia have been suggested, the most common being addressed to the cornea or the sclera. U.S. Pat. No. 6,258,082 describes a method and surgical technique for corneal reshaping and for presbyopia correction. The preferred embodiments of the system consists of a scanner, a beam spot controller and coupling fibers and a basic laser. Presbyopia is treated by a method which uses ablative laser to ablate the sclera tissue and increase the accommodation of the ciliary body.

U.S. Pat. No. 6,263,879 describes treating presbyopia by a method which uses ablative lasers to ablate the sclera tissue and increase the accommodation of the ciliary body. A scanning system is proposed to perform various patterns on the sclera area of the cornea to treat presbyopia and to prevent other eye disorder such as glaucoma.

U.S. Pat. No. 6,491,688 describes a method and apparatus for presbyopia correction. The disclosed preferred embodiments of the system consists of a beam spot controller, a beam delivery device, a slit lamp, a visible aiming beam and a selected solid state laser. Presbyopia is treated by the thermal contraction of the human zonnulas with a temperature increase of about (15-50) degree-C. generated by the selected lasers. The near infrared laser is focused and delivered by a gonio lens to the target zonnulas area and viewed by a surgeon using a slip lamp. The selected laser having optimal absorption characteristics is tightly focused such that only the target zonnulas is heated, while the cornea, the lens body and the adjacent areas are not damaged.

U.S. Pat. No. 6,663,619 (VISX Incorporated) discloses an ophthalmic surgery system and method for treating presbyopia by performing ablative photodecomposition of the corneal surface. A laser system ablates tissue to a predetermined ablation shape, and the cornea heals significantly to form a multifocal shape correcting presbyopia. The multifocal shape corrects for near-vision centrally and far-vision peripherally. The system and method enables wide area treatment with a laser having a narrower beam than the treatment area, and can be used in the treatment of many conditions in conjunction with presbyopia such as hyperopia, hyperopic astigmatism and irregular refractive aberrations.

U.S. Pat. No. 6,745,775 (Surgilight, Inc.) describes treating presbyopia by a method which uses various lasers to remove a portion of the scleral tissue and increase the accommodation of the presbyopic patient's eye.

U.S. Pat. No. 5,312,320 (VISX, Incorporated) describes controlled ablation of the cornea, using ultraviolet laser radiation, wherein irradiated flux density and exposure time are so controlled as to achieve desired depth of the ablation. Sculpturing action results from precharacterized distribution of flux density across the cross-section of laser-beam projection, in the context of beam size, at cornea incidence, to match the area to be ablated, and the duration of exposure determines the extent of curvature change. Illustrative techniques and situations are disclosed, for myopia correction, for hyperopia correction, and for astigmatism correction.

U.S. Pat. Nos. 5,711,762 and 5,735,843 (VISX, Incorporated) describes an argon-fluoride excimer laser or other laser source that directs its radiation through a mask and onto corneal tissue, or other biological matter, to form an ablation therein of predetermined configuration and depth by a process of ablative photodecomposition. The masks are formed with a slit, circular, crescent or other openings of widths between 30 and 800 microns, and may even be formed to provide a graded intensity center to edge. The mask is reflective or composed of or faced with an organic polymer to prevent heat build-up.

U.S. Pat. No. 6,325,792 (Swinger and Lai) describes the application of low energy, ultra-short (femtosecond) pulsed laser radiation to the patient's eye in one of a number of patterns such that the exposed ocular tissue is ablated or excised through the process of optical breakdown or photodisruption in a very controlled fashion. Using the laser inside the eye allows the surgeon to perform glaucoma operations such as trabeculoplasty and iridotomy, cataract techniques such as capsulectomy, capsulorhexis and phacoablation, and vitreoretinal surgery, such as membrane resection. The various procedures are accomplished by controlling energy flux or irradiance, geometric deposition of beam exposure and exposure time.

U.S. Pat. No. 6,706,036 (Lai) describes a laser-based method and apparatus for corneal surgery. The present invention is intended to be applied primarily to ablate organic materials, and human cornea in particular. The invention uses a laser source which has the characteristics of providing a shallow ablation depth (0.2 microns or less per laser pulse), and a low ablation energy density threshold (less than or equal to about 10 $mJ/cm^2$), to achieve optically smooth ablated corneal surfaces. Lai states that the surgical system can be used to perform surgical procedures including removal of corneal scar, making incisions, cornea transplants, and to correct myopia, hyperopia, astigmatism, and other corneal surface profile defects.

U.S. Pat. No. 5,439,462 (Intelligent Surgical Lasers) describes an ophthalmic laser system removing cataractous tissue from the lens capsule of an eye by phacofragmentation of the lens tissue for subsequent aspiration of the treated tissue.

Despite the numerous patents and publications describing treatments for presbyopia, the successful treatment of presbyopia has remained elusive. There remains a need for processes and apparatus for preventing or delaying presbyopia.

SUMMARY OF THE INVENTION

Apparatus and processes are provided for preventing or delaying presbyopia. The process comprises ablating epithelial cells in the germinative zone or the pregerminative zone of the crystalline lens. Preferably, the epithelial cells are ablated symmetrically and/or along suture lines of the crystalline lens and/or by an even number of ablation points. The process can comprise making ablation points symmetrically around the circumference of the crystalline lens. The process can include ablating a desired percentage of the epithelial cells in the germinative zone or the pregerminative zone of the crystalline lens. Using the present apparatus and processes, epithelial cells can be ablated without forming a cataract or an astigmatic condition, and it is not necessary to decrease the equatorial diameter of the crystalline lens.

As another aspect, apparatus and processes are provided for preventing or delaying one or more symptoms of presbyopia in a patient. The process comprises the steps of selecting a patient prior to detecting a symptom of presbyopia in the patient, and ablating epithelial cells in the germinative zone or the pregerminative zone of the crystalline lens. The patient can be selected based on an increased risk factor for presbyopia, such as hyperopia, or based on age, for example wherein the selected patient is less than 40 years of age.

As yet another aspect, a laser apparatus and processes using the apparatus are provided for ablating epithelial cells in a crystalline lens. The apparatus comprises a laser source providing laser light radiation; and a laser delivery system operatively connected to the laser source for receiving the radiation from the laser source and generating a plurality of laser beams. The laser delivery system can include a fiber optic bundle, diffractive optic, binary optic, or other means for providing a plurality of laser beams from a single laser beam. The laser delivery system can also include a focus lens for receiving and focusing the plurality of laser beams. The laser delivery system can include a plurality of primary lenses having different focal lengths and/or a rotator for automatically rotating the plurality of laser beams. The apparatus can also include an alignment mechanism which provides visible light at the ablation points.

DETAILED DESCRIPTION

Figure 1:
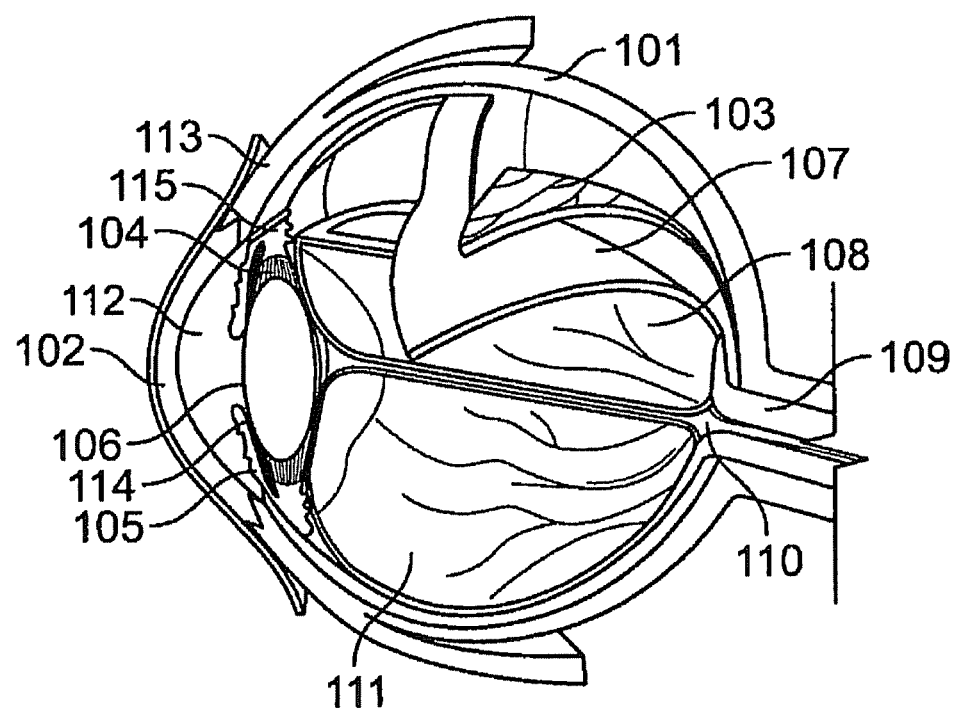
FIG. 1 shows the interior of a human eye, including the crystalline lens.

Apparatus and processes are provided for preventing or delaying the onset or progression of presbyopia. The onset and progression of presbyopia are typically manifested through one or more symptoms of presbyopia, and the present apparatus and processes can be used to prevent or delay one or more symptoms of prebyopia. The apparatus and processes can be used to prevent or delay the onset of presbyopia before a patient is diagnosed with or begins to suffer from one or more symptoms of presbyopia. The apparatus and process can be used to prevent or delay the progression of presbyopia so that one or more symptoms of presbyopia does not become worse or more noticeable.

Symptoms of presbyopia include decreased focusing ability for near objects, eyestrain, difficulty reading fine print, fatigue while reading or looking at an illuminated screen, difficulty seeing clearly up close, less contrast when reading print, need for brighter and more direct light for reading, needing to hold reading material further away in order to see it clearly, and headaches, especially headaches when using near vision.

The apparatus and processes address the onset or progression of presbyopia through the inhibition of epithelial cell reproduction in the crystalline lens. The apparatus and processes can be used to inhibit reproduction of epithelial cells that are about to enter the germinative zone of the crystalline lens. These cells are generally found in a pregerminative zone of the crystalline lens. Alternatively or additionally, the present apparatus and processes can be used to inhibit reproduction of cells already in the germinative zone of the crystalline lens.

Epithelial cell reproduction can be inhibited in a numerous ways. Epithelial cell reproduction can be inhibited by preventing, slowing or stopping epithelial cell mitosis. Reproduction of epithelial cells can be inhibited by ablating epithelial cells in the pregerminative zone or in the germinative zone of the crystalline lens. As described in more detail below, ablation of epithelial cells can promote or establish growth stasis of the crystalline lens. The ablation of epithelial cells is performed in a fashion which avoids, minimizes, or reduces damage to the lens capsule and to epithelial cells in the central zone or to fiber cells.

Epithelial cells in the pregerminative zone and/or in the germinative zone of the crystalline lens can be ablated by any suitable technique, but will generally be ablated using laser-based surgical techniques. Ablating cells means removing cells, including by cutting, extirpating, vaporizing, abrading, or any other suitable technique for removing cells from a living tissue. When using a laser-based surgical technique, ablated cells are usually vaporized.

Treatment processes will generally include the step of dilating the pupil in order to expose more of the crystalline lens. Dilation will facilitate exposure and treatment of the peripheral portions of the crystalline lens, including the germinative zone. Dilation is useful because the present techniques are to be applied to the lens rather than the iris, and the iris normally is disposed above the area of germinative zone and pregerminative zone.

Treatment processes can also include the step of visually identifying the epithelial cells in the germinative or pregerminative zone of the crystalline lens. The epithelial cells can be identified when viewed microscopically by their size or shape. Alternatively the epithelial cells in the germinative zone which are in the process of mitosis can be identified by a biochemical flag or indicator. Accordingly, an additional step may be the administration of such a biochemical flag or indicator.

Treatment processes can also include one or more of the steps of determining the growth rate of a crystalline lens or reproduction rate of epithelial cells in the crystalline lens, and estimating the amount of epithelial cells to be ablated for establishing a growth stasis. If those rates are determined, an approximation can be made regarding the extent to which the mitotic process of epithelial cells should be prevented, slowed or stopped in order to bring to or near a stasis the formation of fiber cells from epithelial cells and/or growth of the crystalline lens.

FIG. 1 shows various structures of the human eye. The outermost layer of the eye is called the sclera 101, which is commonly referred to as "the white of the eye." The sclera 101 is the tough, opaque tissue that serves as the eye's protective outer coat. Tiny muscles connect to the sclera 101 around the eye and control the eye's movements. The sclera 101 maintains the shape of the eye.

The cornea 102 is at the front of the eye. Light passes through the cornea 102 when it enters the eye. The cornea is arranged in layers, namely epithelium, Bowman's layer, the stroma, Descemet's Membrane, and the endothelium. The epithelium is the cornea's outermost region. The epithelium blocks the passage of foreign material, provides a smooth surface that absorbs oxygen and cell nutrients from tears, then distributes these nutrients to the rest of the cornea. The epithelium is filled with thousands of tiny nerve endings that make the cornea extremely sensitive to pain when rubbed or scratched. The present apparatus and processes are designed to avoid damaging or inflicting pain on the cornea (including the epithelium layer). Under the epithelium is a transparent sheet of tissue called Bowman's layer. Bowman's layer is composed of strong layered protein fibers called collagen. If injured, Bowman's layer can form a scar as it heals. If these scars are large and centrally located, some vision loss can occur. Accordingly, the present processes and apparatus are designed to avoid damage to Bowman's layer or other layers containing collagen. Under Bowman's layer is the stroma, which provides most of the cornea's thickness. It is mostly water and collagen. Collagen gives the cornea its strength, elasticity, and form. The collagen's shape, arrangement, and spacing produce the cornea's light-conducting transparency. Under the stroma is Descemet's membrane, a thin but strong sheet of tissue that serves as a protective barrier against infection and injuries. Descemet's membrane includes collagen fibers (different from those of the stroma) and is made by the endothelial cells that lie below it. The endothelium pumps excess fluid out of the stroma. If endothelium cells are damaged by disease or trauma, they are not repaired or replicated. If too many endothelial cells are destroyed, corneal edema and/or blindness may ensue. Once again, the present processes and apparatus are designed to avoid damaging the layers of the cornea (including the endothelial cells of the cornea) when used to treat a patient for the prevention of presbyopia.

Returning to FIG. 1, the choroid 103 (or uveal tract) contains the blood vessels that supply blood to structures of the eye. The front part of the choroid 103 contains: ciliary body 115 which is a muscular area and the zonules 104 that are attached to the lens 114. The ciliary body 115 contracts and relaxes to control the zonules 104, which in turn control the size of the crystalline lens for focusing. The iris 105 is the colored part of the eye. The color of the iris is determined by the color of the connective tissue and pigment cells. Less pigment makes the eyes blue; more pigment makes the eyes brown. The iris is an adjustable diaphragm around an opening called the pupil 106. The iris 105 may be moved by dilating the pupils by administration of eye drops, for example, mydriatics, such as atropine, cyclopentolate, homatropine, phenylephrine, scopolamine, and tropicamide. Ophthalmologists routinely dilate patients' eyes as part of eye exams.

The retina 107 is located at the back of the eye. The retina 107 is the light-sensing portion of the eye. The macula 108 is in the center of the retina, and in the center of the macula is an area called the fovea centralis. This area is responsible for seeing fine detail clearly. Retinal nerve fibers collect at the back of the eye and form the optic nerve 109, which conducts the electrical impulses to the brain. The optic nerve 109 is connected to the sclera 101 at the back of the eye. The spot where the optic nerve and blood vessels exit the retina is called the optic disk 110. This area is a blind spot on the retina because there are no rods or cones at that location.

The eye has two fluid-filled sections separated by the crystalline lens 114. The larger, back section contains a clear, gel-like material called vitreous humor 111. The smaller, front section contains a clear, watery material called aqueous humor 112. The aqueous humor is divided into two sections called the anterior chamber (in front of the iris) and the posterior chamber (behind the iris). The aqueous humor is produced in the ciliary body 115 and is drained through the canal of Schlemm 113. If this drainage is blocked, glaucoma can result.

The crystalline lens 114 is a clear, biconvex structure about 10 mm (0.4 inches) in diameter in an average adult and smaller in children. The crystalline lens changes shape because it is attached to muscles in the ciliary body. The crystalline lens 114 is used for dynamic focusing. Additional details about the crystalline lens are provided in FIGS. 2 and 3 and the descriptions below, as well as in Kuszak et al., *Electron Microscopic Observations of the Crystalline Lens*, Microscopy Research and Technique 33:441-79 (1996) and Kuszak et al., *Biology of the Lens: Lens Transparency as a Function of Embryology, Anatomy, and Physiology*, In: *The Principles and Practice of Ophthalmology* (2nd ed.), edited by Albert DA and Jacobiec F A. Philadelphia, Pa.: Saunders, 1999, p. 1355-1408, both of which are incorporated by reference herein.

The present apparatus and processes primarily relate to the anatomy of the crystalline lens. The adult human crystalline lens is an asymmetric, oblate spheroid. The crystalline lens is an intricate arrangement of highly specialized cells that produce a gradient of refractive index.

Figure 2:
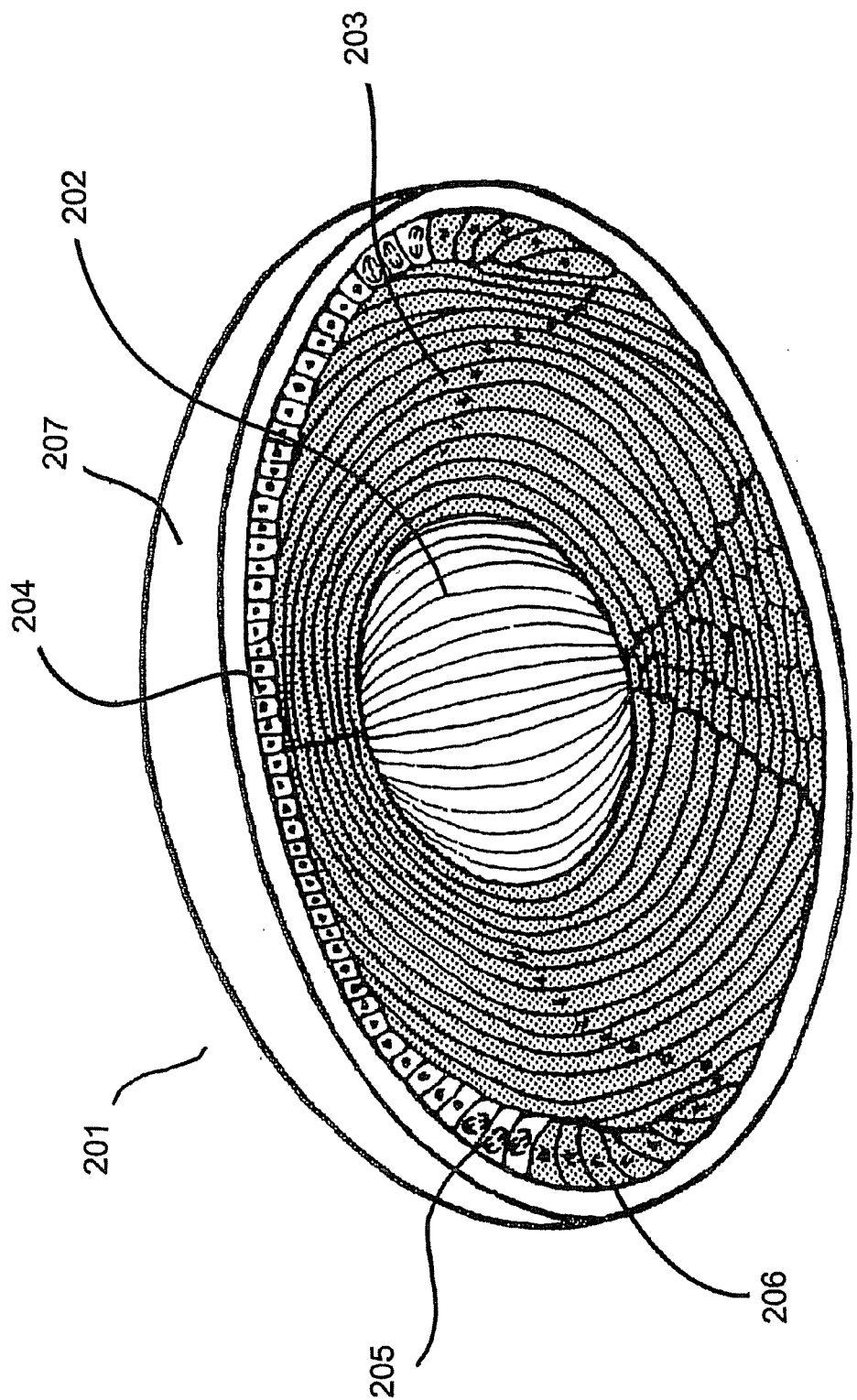
FIG. 2 shows the arrangement of epithelial cells in a crystalline lens of a human.

FIG. 2 shows the general structure of a crystalline lens 201. The crystalline lens is a transparent, biconvex structure with an anterior half that is less spherical, than the posterior half. The core of the crystalline lens comprises a nucleus of primary lens fibers 202 which are elongated along the visual axis. The core is surrounded by a cortex of elongated secondary lens fibers 203. At the anterior face of the lens resides a layer of cuboidal cells 204 which make up the central zone of the lens 201. An anterior monolayer 205 serves as the germ cell layer of the lens, a stratified epithelia-like tissue. However, unlike other stratified epthelia that have their stem cells distributed throughout a basal germ cell layer, stem cells of the lens are sequestered as a narrow latitudinal band within the lens epithelium, forming the germinative zone of the crystalline lens. The germinative zone lies at the periphery of the lens epithelium just above the lens equator. Some of the germinative zone cells undergo mitotic division, and a number of the daughter cells terminally differentiate to become additional lens fibers. Differentiating cells in the process of becoming lens fibers 206 are found outside their germinative zone in the transitional zone. Because these are the second lens fibers to develop, they are referred to as secondary fibers 203. The epithelial cells of the crystalline lens are covered by a noncellular outer covering called the capsule 207.

Figure 3:
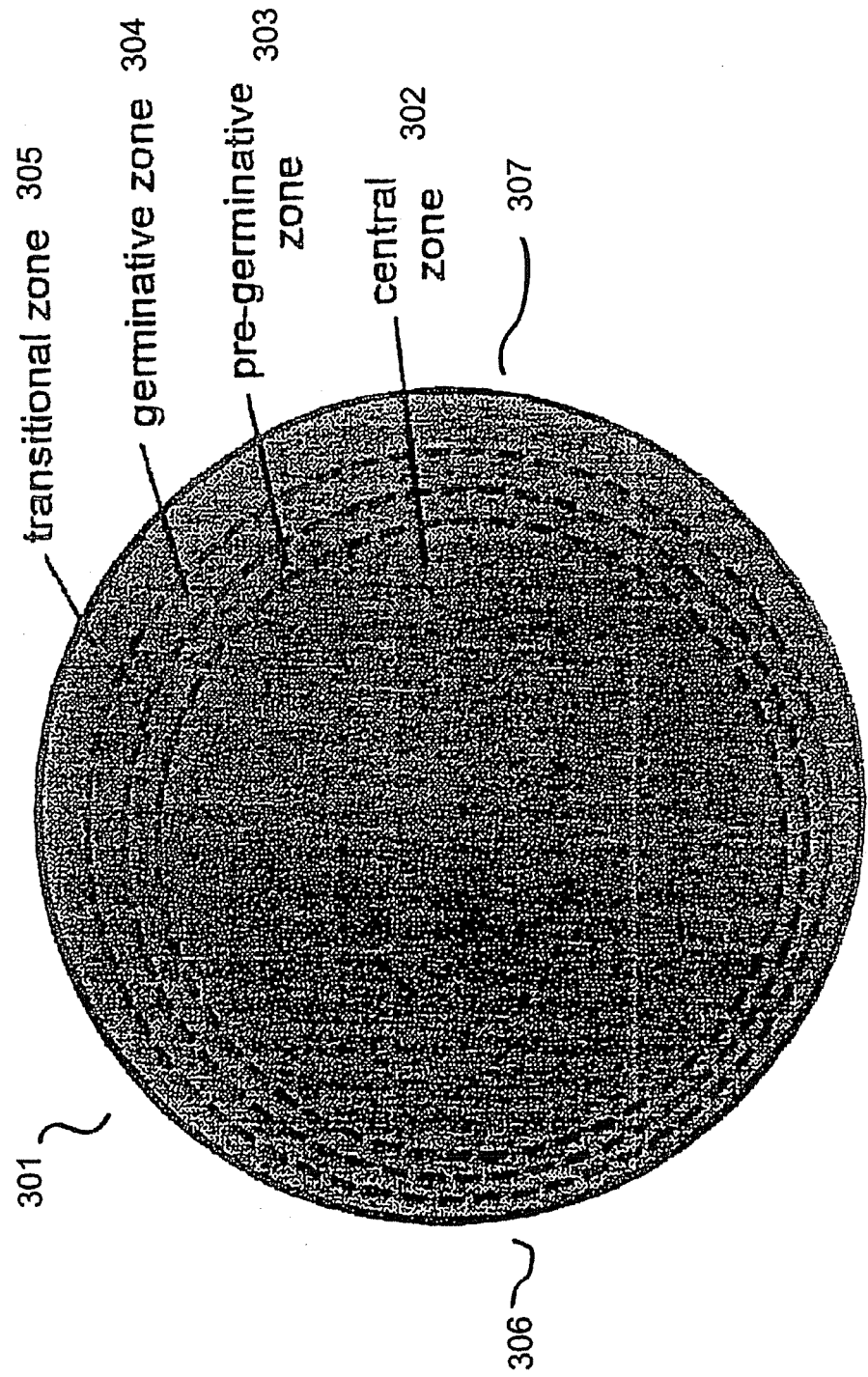
FIG. 3 shows the various zones of epithelial cells in a crystalline lens.

FIG. 3 generally shows that the lens epithelial cells tend to be sequestered in distinct zones within the lens epithelium. A central zone 302 comprises a broad polar cap of lens epithelium that covers most of the anterior surface of the lens. Central zone cells are held in the G0 stage of, the cell cycle and, therefore, do not contribute to secondary fiber formation. Between the central zone 302 and the germinative zone 304 is a relatively narrow zone called the pregerminative zone 303. A small number of pregerminative zone cells undergo mitosis, and some of these daughter cells terminally differentiate into secondary lens fibers. Finally, beyond the germinative zone is a narrow latitudinal band of cells called the transitional zone 305. Transitional zone cells are the cells that have undergone mitosis in the germinative zone and have been selected to terminally differentiate into secondary lens fibers. As additional germinative zone cells are recruited throughout life to become secondary lens fibers, the transitional zone cells are forced to migrate posteriorly. During the migration of these nascent secondary lens fibers, they simultaneously rotate 180 degrees about their polar axis, and then elongate bidirectionally until they become mature secondary lens fibers. As elongation proceeds, the anterior ends of the initial elongating secondary lens fibers are insinuated beneath the apical membranes of the overlying lens epithelium and above the anterior ends of the primary lens fibers. Simultaneously, the posterior ends of the same elongating secondary lens fibers are insinuated beneath the lens capsule and above the posterior ends of the primary lens fibers. Secondary lens fiber elongation is complete, and fibers are considered mature when they are arranged end to end as a complete growth shell, rather than as a layer or stratum, as is typical of most stratified epthelia.

As additional secondary lens fibers develop throughout life, their anterior ends are insinuated beneath the apical membranes of the lens epithelium and above the anterior ends of previously formed lens fibers, while their posterior ends are insinuated above the capsule and beneath the basal membranes of the same previously formed lens fibers. The ends of the lens fibers meet to form a definitive line called a suture line. In this manner, lens fibers of every shell lie atop lens fibers of the previously formed shell and beneath the lens fibers of the subsequently formed shell. In addition, the entire lens mass is enclosed in a basement membrane-like capsule, that is produced by the basal membrane of the lens epithelial cells and elongating lens fibers. As a result of its continuous production throughout life, the lens capsule becomes the thickest basement membrane in the body.

Unlike other stratified epithelia, the crystalline lens does not routinely slough off cells from its older, uppermost strata. Instead, the older lens cells are progressively more internalized throughout life. In this manner, the crystalline lens retains all of its lens fibers arranged in order of ascending age from its periphery to its interior.

At any age, the germinative zone 303 comprises approximately the outer 10% of the anterior surface of the lens epithelium (additionally, the transitional zone comprises the most peripheral segment of this area). The central zone 302 and pregerminative zone 304 account for the remaining 90% of the anterior surface area of the lens epithelium. Although all zones of the lens epithelium increase in size as a function of age, mitotic activity is restricted primarily to the germinative zone.

As mentioned above, lens epithelial cells are separated into distinct subpopulations. Adult lens central zone epithelial cells are cuboidal 204 with an average height of 3 to 7 μm. Pregerminative zone cells and germinative zone cells are generally smaller. The germinative zone may be identified on the crystalline lens by reference to latitudinal and longitudinal coordinates, for example, from 90 degrees (the top of the crystalline lens) to about 75 to about 80 degrees latitude is the central zone. The germinative zone is from about 0 degrees to about 10 degrees latitude. The longitudinal coordinates can be between 0 and 90 degrees, though preferably symmetrical longitudinal coordinates are employed.

The proliferation of fiber cells in the crystalline lens can be reduced by preventing, slowing or stopping the mitotic process of epithelial cells before or after they enter the germinative zone, such as by ablating such epithelial cells. If the mitotic process of a significant percentage of epithelial cells is prevented, slowed or stopped, the epithelial cells form fewer fiber cells, and growth of the crystalline lens can be brought to or near a stasis. Moreover, by inhibiting the mitotic process, the compaction of epithelial cells within the crystalline may be reduced or slowed. These effects can prevent or delay the onset or progression of one or more symptoms of presbyopia.

Ablation of epithelial cells in the germinative zone or the pregerminative zone according to the present techniques does not require a decrease the equatorial diameter of the crystalline lens, but rather promotes or establishes growth stasis of the crystalline lens and may also reduce the compaction of fiber cells in the cortex and/or nucleus of the crystalline lens. Preferably epithelial cells are ablated so as to promote or establish growth stasis in the crystalline lens, to avoid or reduce or minimize compaction of the fiber cells of the cortex and/or nucleus of the crystalline lens, and/or to maintain the size of the crystalline lens. In some embodiments, the process for preventing or delaying the symptoms of presbyopia can include ablating epithelial cells in the crystalline lens without stopping growth of the crystalline lens; that is, the crystalline lens may continue to experience some growth and become somewhat larger, but the symptoms of presbyopia are prevented or delayed.

The present processes are primarily designed to symmetrically ablate epithelial cells in the pregerminative zone and/or in the germinative zone of the crystalline lens. When an ablative point is made on the crystalline lens, preferably there is also one or more additional ablation points made to form a symmetric pattern with the first (and any other) ablation point, such that the ablation points are symmetrically disposed around the crystalline lens (more particularly, around the pregerminative zone or the germinative zone of the crystalline lens).

While some types of laser surgery may employ either an even or odd number of ablation points (for example, providing holes in the iris for relieving pressure for glaucoma), it is contemplated that an even number of ablation points can be preferable for the present processes. Where a number of ablation points are made in the crystalline lens, it is desirable that the ablation pattern is symmetrical and that the number of degrees between each ablative point is approximately the same.

It is desirable in the present processes to provide symmetrical ablation of epithelial cells in the germinative zone and/or the pregerminative zone of the crystalline lens. This is in contrast to other types of ophthalmic surgery, where symmetry is not as important or immaterial. This is because when lens cells are damaged, cells or fiber growth will move toward the damaged area, which may result in disruption of visual clarity. By symmetrically ablating the epithelial cells, movement of cells and fiber growth will tend to be relatively uniform in the crystalline lens, which should avoid or reduce disruption of visual clarity.

Accordingly, the present processes will preferably yield an even number of ablation points (although an odd number may be suitable in some circumstances). More preferably the present processes yield a symmetric pattern of an even number of ablation points around essentially the entire circumference of the crystalline lens. For example, if six ablation points were to be made in the crystalline lens at various degrees longitude, ablation points could be made at 90 degrees, 91 degrees, 92 degrees, and at 270 degrees, 271 degrees, and 272 degrees, because that would result in having three ablation points on either side, though the regions at zero degrees and 180 degrees would not be ablated. However, it would be more desirable to have the ablation points at 0 degrees, 60 degrees, 120 degrees, 180 degrees, 240 degrees, and 300 degrees, so that the ablation points were symmetrical around the entire circumference of the crystalline lens.

Preferably, the epithelial cells are ablated symmetrically around the crystalline lens and/or an even number of ablation points are made. For example, at least 4 symmetrical ablation points are made in the crystalline lens, such as at about 0 degree longitude, about 90 degrees longitude, about 180 degrees longitude, and about 270 degrees longitude around the circumference of the germinative zone or the pregerminative zone. As another example, at least 12 symmetrical ablation points are made in the germinative zone of the crystalline lens, such as at about 0 degree, about 30 degrees, about 60 degrees, about 90 degrees, about 120 degrees, about 150 degrees, about 180 degrees, about 210 degrees, about 240 degrees, about 270 degrees, about 300 degrees, and about 330 degrees (all in degrees longitude), around the circumference of the germinative zone or the pregerminative zone.

By using symmetric ablation, it is believed the risk of causing a cataract or an astigmatic condition is reduced. A cataract is a clouding of the crystalline lens. An astigmatic condition would occur where the crystalline lens distorts because the progression of epithelial cells around the circumference of the crystalline lens has not been uniformly slowed or stopped. By using symmetric ablation, it is believed that the likelihood of maintaining optical clarity of the crystalline lens is improved.

It is desirable to make ablation spots in a manner which maintains optical clarity of the crystalline lens. To that end, it is desirable to maintain fiber cell growth toward the suture lines which are naturally present in the crystalline lens and to avoid growth of the fiber cells in a different or haphazard fashion. Suture lines are the end-to-end junctions of the fiber cells which are aligned with each other. One technique for improving the likelihood of maintaining fiber cell growth toward suture lines is to ablate epithelial cells along the suture lines of the crystalline lens.

Ablating epithelial cells in a symmetrical pattern and/or along suture lines reduces the risk that other epithelial cells will repair perceived damage from ablation in a manner which interferes with optical clarity. Although the present processes is designed to ablate epithelial cells before differentiation, fibers in the process of differentiating rely on epithelial cells for critical information. Moreover, ablating some epithelial cells can decrease the provision of differentiation support factors, thereby reducing the reproduction and/or differentiation of unablated epithelial cells.

The present processes may comprise making a number of ablation points in the epithelial cells of the germinative zone or the pregerminative zone of the crystalline lens to prevent or delay the onset or progress of presbyopia or one or more symptoms. The epithelial cells can be ablated by making a suitable number of ablation points in the germinative zone or in the pregerminative zone, for example 2, 3, 4, 6, 8, 12, 16, 20, 24, 28, 30, 60, 120, 180, 360, 480, 540, 600, 660, 720, 800, 840, or 960 ablation points are made in the germinative zone or the pregerminative zone of the crystalline lens. Furthermore it may desirable to make even larger numbers or ablation points of ablation points in the germinative zone or in the pregerminative zone, for example about 1000, 1800, 2000, 2400, 3000, 3600, 4000, 4800, 5000, 6000, 7000, 7200, 8000, 8800, 9000, 9600 or 10000. Any two of the foregoing numbers may be combined to form a range of ablation points.

Preferably, epithelial cells in the germinative or pregerminative zone are sufficiently ablated so that growth stasis of the crystalline lens is established. Alternatively, epithelial cells in the germinative or pregerminative zone are sufficiently ablated to establish a growth rate that is about 95% or less of the pre-ablative growth rate, alternatively about 90% or less. Alternatively, epithelial cells in the germinative or pregerminative zone are sufficiently ablated to establish a growth rate that is at most about 85%, 80%, 75%, 70%, 65%, 60%, 55%, 50%, 45%, 40%, 35%, 30%, 25%, 20%, 15%, 10%, 5%, 3%, 2%, or 1% of the pre-ablative growth rate.

The present processes comprise making a sufficient number of ablation points without ablating so many epithelial cells that the function or structure crystalline lens is seriously damaged, such as by the formation of a significant cataract or astigmatic condition. It is contemplated that not each and every epithelial cell in the germinative zone will be ablated, but rather a percentage of such cells. In preferred embodiments, at least about 10% of the epithelial cells in the germinative zone of the crystalline lens are ablated. Alternatively, at least about 0.001%, at least about 0.01%, at least about 0.1%, at least about 1%, at least about 2%, at least about 5%, at least about 7%, at least about 10%, at least about 12%, at least about 15%, at least about 18%, at least about 20%, at least about 25%, at least about 30%, at least about 35%, at least about 40%, at least about 50%, at least about 60%, or more of the epithelial cells in the germinative zone and/or the pregerminative zone of the crystalline lens are ablated. Alternatively a percentage of the circumference of the germinative or pregerminative zone may be ablated. For example, from about 0.001% up to 100% of the circumference of the crystalline lens can be ablated.

The number of ablation points made in the present processes will depend in part on the size and shape of the ablation points. For example, fewer ablation points will usually be made when the ablation points are larger. Sizes for the ablation points include, but are not limited to, ablation points having diameters in the range from about 1.6 microns to about 3000 microns, alternatively from about 3 microns to about 1000 microns, alternatively from about 3.12 microns to about 106 microns. Preferably, ablations points have diameters sizes in the range of from about 3 to about 300 microns. Sizes for ablation points further include, but are not limited to, ablation points having volumes in the range of from about 14 cubic microns to about $1.4 \times 10^7$ cubic microns, alternatively from about 140 cubic microns to about $1.4 \times 10^6$ cubic microns, alternatively from about 1400 cubic microns to about $1.4 \times 10^5$ cubic microns. The ablation points can have a shape that is round, square, polygonal, or another shape. For example, the ablation points may have the shape of a circle, curved line or crescent, which may facilitate ablation of a larger number of epithelial cells at each ablation point. The ablation points can be connected to form a larger and/or different shape or pattern. For example, the ablation points can be connected to form a line, a ring, or circle that is essentially the entire circumference of the crystalline lens.

The processes may further comprise the step of selecting a patient(s) prior to the onset of one or more symptoms of presbyopia, and ablating a number of epithelial cells in the germinative zone or in the pregerminative zone of the crystalline lens of the selected patient(s). A number of epithelial cells are ablated to prevent or delay one or more (preferably all) symptoms of presbyopia. The patient may be selected based on age or based on one or more risk factors for symptoms of presbyopia. For example, the patient may be at least 12 years of age, alternatively at least 15 years of age, alternatively at least 18 years of age, alternatively at least 21 years of age, alternatively at least 25 years of age, alternatively at least 30 years of age, alternatively at least 35 years of age, alternatively at least 40 years of age, alternatively at least 45 years of age, alternatively at least 50 years of age, alternatively at least 55 years of age, alternatively at least 60 years of age, alternatively at least 65 years of age, alternatively at least 70 years of age, alternatively at least 75 years of age, alternatively at least 80 years of age. Alternatively, the patient may be less than 12, 15, 18, 21, 25, 30, 35, 40, 45, 50, 55, 60, 65, 70, 75, or 80 years of age. The patient may be selected based on an increased risk factor for symptoms of presbyopia, such as hyperopia (which puts additional demand on the flexibility of the lens), occupation (which is a risk factor if the occupation requires near vision demands), gender (presbyopia often occurs earlier in females, ocular disease or trauma (damage to the lens or ciliary muscles can accelerate progression of presbyopia), systemic disease (diabetes and multiple sclerosis increased risk for presbyopia), drug use (drugs such as alcohol, antidepressants, and antihistamines can decrease the flexibility of the lens), or atmospheric or geographic factors (higher annual temperatures and greater exposure to ultraviolet radiation put individuals at an increased risk for presbyopia).

The present apparatus and processes include several techniques for inhibiting epithelial cell mitosis, specifically mitosis of those cells that are in the germinative zone of the crystalline lens. For example, a laser-based approach may be used wherein a laser is employed to inhibit epithelial cell mitosis ablating by those lens epithelial cells that are becoming mitoticly active. Those epithelial cells are generally located in the germinative zone of the lens.

The present apparatus will include a laser source capable of generating a laser beam. Preferably, the laser source generates short pulses of laser light having a wavelength which will not damage the cornea and which will not generate substantial thermal damage to the eye. In general, the energy level per pulse for the laser is preferably in the range of from about 0.1 microjoules to about 1200 microjoules, preferably from about 1 microjoule to about 120 microjoules, more preferably about 12 microjoules. Numerous commercially available lasers meet these requirements. Using lasers at very short pulse durations with a relatively predictable power level is desired, so if the laser is well calibrated, there should not be significant differences in the amount of energy provided for each ablation point.

Preferred laser sources include sources of visible wavelength laser light and infrared laser light. Preferably, a YAG laser is used, such as a Nd:YAG (Neodymium:Yttrium Aluminum Garnet) laser. Ophthamic Nd:YAG lasers for laser capsulotomy after cataract surgery include the 7970 Coherent YAG laser; Ophthalmic Nd:YAG laser YC-1600 available from Nidek Incorporated of Fremont, Calif.; and the Alcon 2500 YAG Laser. Nd:YAG lasers have been used for ophthalmological surgeries such as posterior capsulotomy and peripheral iridotomy. Nd:YAG lasers generate short pulse, low energy, high power, coherent optical radiation. When the laser output is combined with focusing optics, the high irradiance at the target causes tissue disruption via optical breakdown. Different materials can be included in the YAG crystals that emit very specific wavelengths. In medical applications, homium and thulium are impurities frequently used in the YAG crystal, but they have slightly different wavelengths.

Other laser sources include helium-cadmium lasers, argon ion lasers, krypton ion lasers, xenon lasers, iodine lasers, holmium doped yttrium-aluminum garnet lasers, yttrium lithium fluoride lasers, excimer lasers, chemical lasers, harmonically oscillated lasers, dye lasers, nitrogen lasers, neodymium lasers, erbium lasers, ruby lasers, titanium-sapphire lasers and diode lasers. Suitable YAG lasers further include frequency doubled and frequency tripled YAG lasers. The wavelength of many YAG lasers can be converted from infrared to the green or UV part of the spectrum, by shining them through special crystals. Because these are conversions from the original infrared wavelength to the second or third harmonic of the fundamental frequency, suitable additional ranges of laser light wavelengths are provided.

A laser source provides a beam with a characteristic power, which depends on the wavelength of the laser light radiation. The laser beam also has a diameter and a surface area of contact. For example, if the diameter of the beam is 1.17 cm, the illuminated surface area will be one square centimeter, since the area is determined by the equation $\pi r^2$ where r is the radius of the beam. If a laser source provides a laser beam having a power of 1 watt and a diameter of 1.17 cm, the beam has an irradiance or intensity of 1 watt per square cm, since the intensity is determined by the equation $I=P/A$, where P is equal to Power (in watts) divided by A, the area illuminated by the beam in square centimeters. Therefore, if a beam having a power of 1 watt had a diameter of 0.56 cm, the irradiance would be 4 watts/square cm, since the surface area illuminated would be 0.25 $cm^2$.

If this same laser beam was focused with a focus lens to a smaller diameter and surface area, the intensity would be greatly increased. For example, if the same beam (having a power of 1 watt) were focused to a diameter of $15.7 \times 10^{-11}$ square cm, the intensity would be 1 watt/$15.7 \times 10^{-11}$ square cm, or 6.37 million watts/square cm. From these calculations, it can be seen that laser beams having relatively low laser power are capable of producing high intensities when focused. For that reason, many laser delivery systems include focus lens(es) to adjust the size and intensity of laser beams.

For the present apparatus, the laser source and laser delivery system should be selected and operated in a manner that avoids, reduces or minimizes damage to the cornea. The wavelength of the laser light can be a wavelength that is generally not absorbed by the cornea. Wavelengths of about 400 nm and longer, alternatively about 632 nm and longer, are preferred. Wavelengths of about 1400 nm and shorter are also preferred. The laser delivery system can include a focus lens that focuses the laser beam at a desired point of ablation rather than at another part of the eye.

All materials have a damage threshold, which is a level at which the intensity of the laser beam will cause the material to begin to vaporize or burn. The threshold is the level where damage begins to occur. For materials at room temperature, the damage threshold is dependent upon the intensity of the laser light, how long the light is illuminating the area, and the amount of laser light absorbed by the material.

When a laser beam contacts a material, the material may absorb the radiation and convert it to heat. The amount of energy from the laser beam absorbed by the material and converted to heat is partially dependent upon the wavelength of the laser beam. In the case of eye tissue, wavelengths in the visible part of the electromagnetic spectrum (from about 400 nm to about 700 nm) readily pass through the cornea and the crystalline lens and are absorbed at the retina. If the corneal and crystalline lens tissues are healthy, a very small percentage of laser energy is absorbed by them. However, at wavelengths shorter than 400 nm (which is the ultraviolet part of the spectrum), the tissue that makes up the cornea and crystalline lens absorb higher percentages of energy. This is also true for wavelengths longer than 700 nm. The near infrared part of the spectrum (from about 700 to about 1400 nm), although not visible to the naked eye, can pass through the cornea and lens, but again, with higher levels of absorption than visible light. Wavelengths longer than about 1400 nm are, for the most part, completely absorbed by the cornea. The Nd:YAG laser operates at 1064 nm in the near infrared part of the spectrum. Therefore, a this wavelength, some absorption occurs in the corneal and lens tissues.

As discussed above, the intensity of the laser increases as the area illuminated decreases. A focus lens used for focusing light has a specific focal length for a given wavelength of light. The focal length of a lens refers to the distance from the lens that the light will converge to the smallest diameter before diverging, or spreading out again. This is often referred to as Best Focus of the lens because it is the best or smallest spot which the focus lens can make under the given conditions.

After a laser beam (or more generally, any light) passes through a focus less, the diameter of the laser beam exiting the focus lens gets smaller and smaller until it reaches the Best Focus. For example, a YAG laser beam with a diameter of about 10 mm is pointed directly at the center of a lens with a nominal focal length of 50 mm. If the beam is measured at a distance of 25 mm after that focus lens, the beam is about 5 mm in diameter. In other words, at half the distance to best focus (25 mm away from a lens having a 50 mm focal length), the beam is half its original diameter. At a distance of 37.5 mm from the lens, the beam is about 2.5 mm in diameter. At a distance of 43.75 mm from the lens, the beam has a diameter of about 1.25 mm. At a distance of 46.875 mm from the lens, the beam diameter is about 0.625 mm (625 microns). At a distance of 48.4375 mm from the lens, the beam is about 312 microns in diameter. This reduction continues down to best focus where it produces a focus spot approximately 3.2 microns in diameter (having an area of approximately 10.24 square microns) at a distance of 50 mm from the lens. It is not presently possible to obtain a focus spot of less than about 3 times the wavelength of the light being focused. For an Nd:YAG laser at 1.064 microns, the best focus would be about 3.2 microns.

Figure 10:
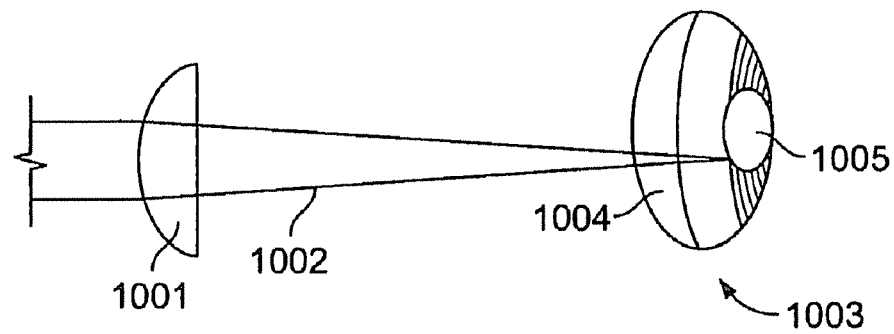
FIG. 10 shows how laser light radiation is focused at an ablation point on a crystalline lens rather than a cornea.

FIG. 10 illustrates how the distance from the focus lens can be used to selectively ablate epithelial cells of the crystalline lens without damaging the cornea or lens capsule. In the illustration, a focus lens 1001 focuses a laser beam 1002 that contacts an eye 1003. The focus lens is positioned to that its "best focus" will be at the epithelial cells of the crystalline lens 1004. At the surface of the cornea 1004, the laser beam has a diameter of about 312 microns. At the crystalline lens 1005, however, the laser beam has a diameter of about 3.12 microns. With a one watt laser, the intensity would be 1309 watts/square cm at the surface of the cornea, and 40 million watts/square cm at the lens tissue. This is because the surface of the cornea is physically further away from best focus. While a distance of 1.5 mm may not seem like a long distance, it is a significant distance in this context, near the best focus of a focus lens having a focal length of 50 mm. Although the distance that separates the two tissues (1.5 mm) is relatively small, the intensities of the laser beam at these two planes are significantly different.

The value of 1.5 mm for separation from the surface of the cornea to the lens tissue is used as an example, and the actual separation for a patient may vary slightly. Accordingly, it is contemplated that the present apparatus and processes may also steps or apparatus for measuring the separation, particularly the thickness of the cornea, and adjusting the ablation or laser delivery system based upon the measured thickness. Suitable techniques for measuring corneal thickness include an optical low coherence reflectometry (OLCR) pachymeter or an ultrasonic pachymeter.

Even if cornea and the crystalline lens tend to absorb the laser light, the cornea is able to dissipate the absorbed laser energy as heat without damage, since the laser light has an intensity (about 1309 watts/square cm) which is below the damage threshold of the cornea tissue. However, at about 40 million watts/square cm, the epithelial cells of the crystalline lens are vaporized because the damage threshold of that tissue has been exceeded. In short, by positioning the focus lens a precise distance from the crystalline lens in the eye, the present processes and apparatus can ablate epithelial cells without damaging the cornea.

When the damage threshold of a tissue has been exceeded, tissue is ablated and form a cloud of vaporized material. A percentage of laser light is absorbed in the vaporized tissue. This means that a portion of a laser pulse may tend to heat the vaporized material, creating a plasma. This would be seen as a flash of white light at or near best focus. The plasma continues to heat and expand, vaporizing more surrounding tissue as long as the laser pulse continues to heat it. The heat generated by the plasma interacts with the lens tissue differently than the pure laser light does and tends to heat the surrounding lens tissue which creates more thermal damage than vaporization. However, by limiting the length of the laser pulse in time, it is possible to minimize the undesired thermal damage by reducing the amount of remaining laser energy that tends to heat the plasma that formed by the leading edge of the pulse. Laser beams having pulse lengths below about 1 microsecond tend to be more ablative than thermal. Shorter pulse lengths tend to do less thermal damage, but require higher average power from the laser to produce the desired ablation. Accordingly, it is desirable to provide a laser beam having a sufficiently high intensity to ablate epithelial cells in a relatively short pulse. For example, pulse durations of about 100 microseconds or less, alternatively about 10 microseconds or less, alternatively about 1 microsecond or less, alternatively about 100 nanoseconds or less, alternatively about 10 nanoseconds or less, alternatively about 1 nanosecond or less, alternatively about 100 picoseconds or less, alternatively about 1 picosecond or less, alternatively about 100 femtoseconds or less, alternatively about 10 femtoseconds or less are contemplated.

The present apparatus may include a laser source which provides laser light in pulses. The laser source may include a laser-generating element that produces pulses of laser light having a selected pulse length and/or pulse rate. Pulses can be generated by a laser internally using various methods, such as by pulsing the excitation mechanism or Q-switching, or the laser can be run in a continuous wave (CW) mode and modulated externally using deflectors or modulators such as acousto-optic or electro-optic types. The laser source may include a pulse-selection element operatively coupled to the laser-generating element, such as when the laser-generating element produces a continuous beam of laser light rather than a pulse or produces pulses which are different from what is desired. Suitable pulse-selection elements are commercially available from Neos Technologies and Intra-action Corporation. The pulse length and pulse rate are selected in conjunction with laser wavelength and energy level so that the application of laser light ablates the desired epithelial cells without unduly damaging surrounding tissue or the cornea. Any suitable pulse length may be employed in the present processes and apparatus. Laser light may be applied to the crystalline lens in pulse(s) having a length on the order of nanoseconds, for example, tens or hundreds of nanoseconds. Alternatively, the pulse length may be on the order of microseconds, picoseconds, or femtoseconds. With a femtosecond laser, each pulse of laser light has a pulse length on the order of femtoseconds (or quadrillionths of a second).

Short pulse lengths are desirable to avoid transferring heat or shock to material being lasered, which means that ablation can be performed with virtually no damage to surrounding tissue. Further, a femtosecond laser can be used with extreme precision. Femtosecond pulse generating lasers are known to the art. Lasers of this type are capable of generating pulse lengths presently as short as 5 femtoseconds with pulse frequencies presently as high as 10 KHz.

While the present processes may be applied using conventional laser equipment as described above, novel laser-based surgical apparatus can facilitate the inventors have also developed. A laser source such as a Nd: YAG laser source can be operatively coupled to laser delivery system that generates a plurality of laser beams, so that a plurality of ablation points on the crystalline lens may be generated simultaneously. The laser source can include the lasing medium, electronic controls, power supply and internal optics for pulsed or continuous wave operation; the laser source provides a beam to external components which may include lenses, or more mirrors and beam splitting optics to couple the laser energy to the laser delivery system. For example, the laser beams may be generated by a fiber optic bundle, a diffractive optic, or a binary optic. Fiber optic bundles are groups of optical fibers bound together, typically at the ends only, and encased in a flexible protective jacket. The ends of a fiber optic bundle can include almost any number of optical fibers and can be arranged into different shapes and configurations.

In addition to a suitable laser source, the laser apparatus also comprises a laser delivery system which provides a plurality of laser beams. The laser delivery system may include a fiber bundle, diffractive optic or other discrete components for generating multiple beams and any mechanical apparatus for holding, rotating or positioning elements of the delivery system. The laser delivery system can also include a beam intensity controller which can regulate the energy of each laser pulse so that the ablation as another way controlling ablation. The laser source and/or laser delivery system can be operatively connected to a computer controller which is programmed to control the generation of laser beams. The computer controller can be connected to the focus lens and programmed to move the focus lens to provide a precise change in the separation of ablation points.

Figure 4:
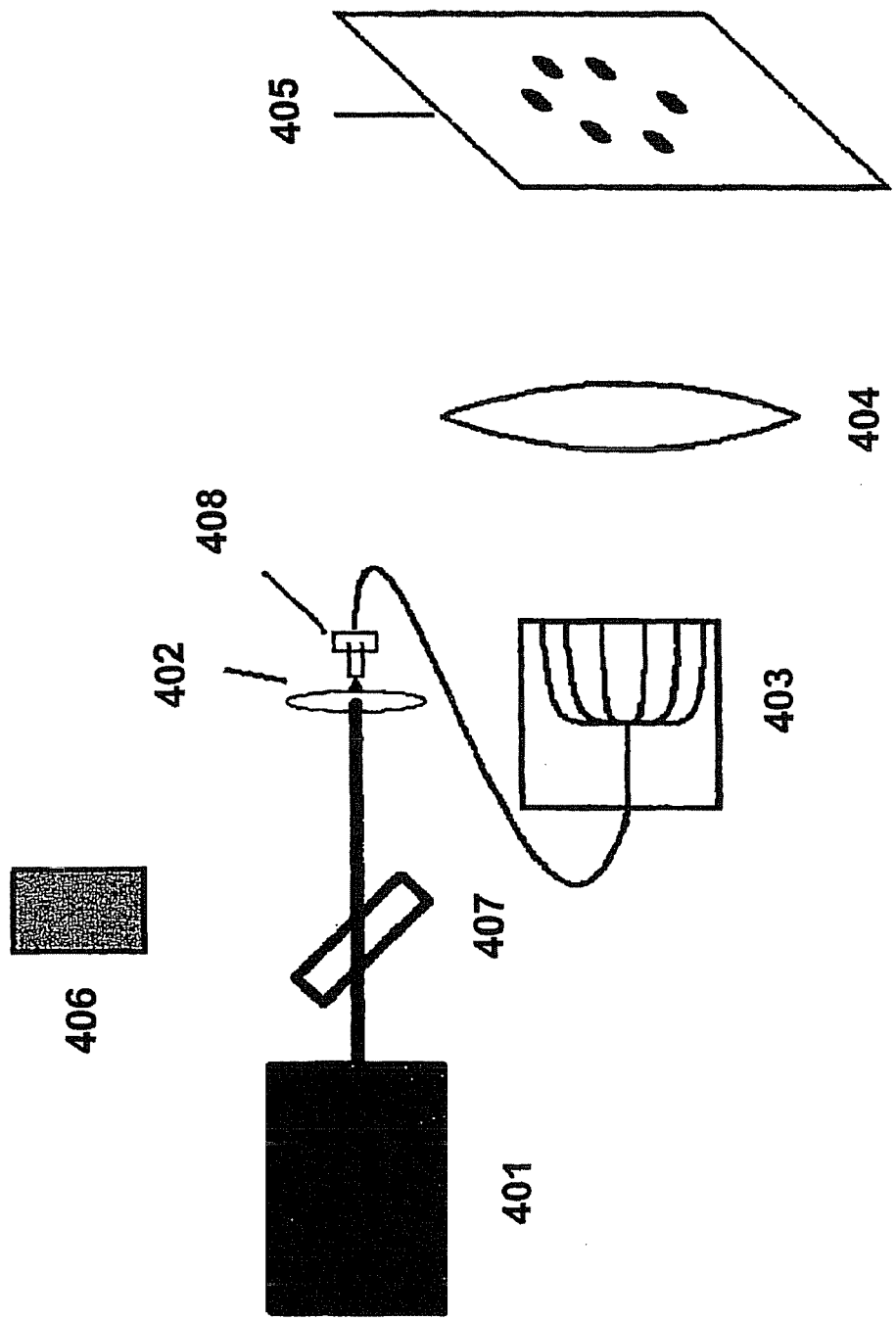
FIG. 4 show a laser system using a laser bundle for ablating a large number of epithelial cells in a desired location.

FIG. 4 illustrates a laser apparatus in which laser light radiation (a laser beam) from a laser source 401 is transferred into the proximal end of a bundle of single mode fiber optics using a positive lens, referred to herein as a launching lens 402. The distal end of optical fiber bundle 403 of this laser delivery system provides a plurality of laser beams. Single mode optical fibers typically have core diameters of 9 microns or less, allowing only one type of laser energy distribution to propagate through them. The number of optical fibers in the bundle can vary. Each optical fiber will receive a portion of the total energy from the laser source. Consideration for the amount of energy required for the treatment process from each optical fiber, the amount of available energy from the laser and the potential damage threshold of the proximal end of the optical fibers are factors in how many actual fibers are used. For this example, six individual optical fibers are represented. A modified version of this would be to launch the laser energy into a single optical fiber. This optical fiber would then be split into two optical fibers. The two optical fibers are then split again to give four optical fibers. This process can be continued to achieve the desired number of optical fibers at the distal end. This process is preferred for more uniform laser intensity at each distal end of the optical fibers.

At the distal end 403 of the fiber optic bundle, each optical fiber is separated and positioned in a holder made of a material that will set the position and separation of each optical fiber end with respect to each other and allow for the polishing of all the optical fibers as a unit. Materials such as, but not limited to, aluminum, nylon or plastic for example, may be used to join the optical fibers into a fiber optic bundle. The ends of the optical fibers are typically affixed using a suitable epoxy. Energy launched into the proximal end of the fiber optic bundle will exit the distal ends and propagate towards the primary focus lens. The distance from the distal end of the fiber optic bundle to the primary focus lens should be such that all laser energy from the sum of the optical fibers falls within the clear aperture of the lens to minimize loss.

Figure 8:
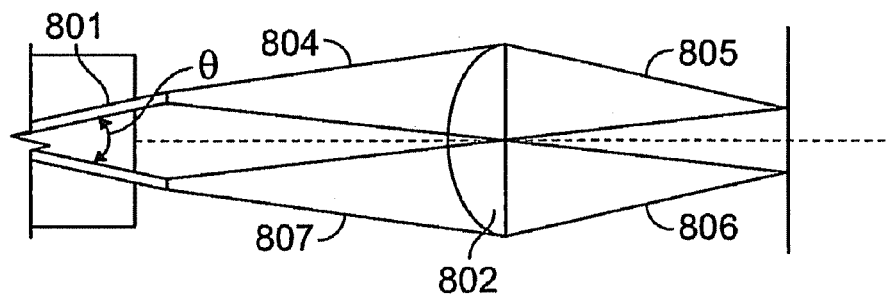
FIG. 8 shows how a focus lens can provide ablation points of a desired size or at a desired distance from laser light radiation provided by a fiber optic bundle.

The laser delivery system of FIG. 4 also includes a focus lens 404. The primary focus lens will image the laser light from the fibers at the focal length of the primary focus lens. The focused laser beams will form spots at Best Focus in an image plane 405. For example, if the ends of 9 micron core optical fibers are separated radially on a 3.75 mm diameter, the primary focus lens will produce an image of approximately 9 micron spots with the same relative separations at the focus of the lens. This is an example of 1:1 image relay. Altering the focal length of the primary focus lens can effect the separation of the spots produced. FIG. 8 illustrates how a pair of optical fibers 801 offset from each other at an angle θ (theta) can interact with a focus lens 802 downfield from the optical fibers 801. The optical fibers 801 emit laser beams 804 and 807 which pass through and are focused by the focus lens 802. Each of laser beams 804 and 807 contacts the focus lens 802 at an angle off-center. The focus lens 802 provides beams 805 and 806 whose diameters are narrowing and whose irradiance is increasing as they approach a focal point. The focus lens 802 can be computer-controlled and/or motorized so that the distance from the optical fiber can be adjusted, thereby adjusting the separation between the ablation points. The motor actuation of the focus lens can be done by any means, such as electrical gear devices or piezoelectric activators.

The fiber optic bundle can be held in a mechanical stage that can rotate the device, for example, along the 3.75 mm diameter in which the fiber end lie. This allows for the spots being imaged on the eye tissue to rotate as well. It also allows for the illumination of new tissue for therapy along a fixed diameter. This rotational device can be manual or motorized. These devices can be equipped with digital readouts that can give rotational information of the fiber optic bundle or the diffractive optic with a high degree of accuracy which directly correlates to the rotation of the focus spots in the circular pattern.

A visible aiming system can be utilized to target the invisible Nd:YAG laser radiation on or in close proximity to the germinative zone or another target zone. FIG. 4 also shows how visible laser energy that is below the damage threshold of eye tissue can be introduced into the fiber optic bundle device using an alignment mechanism which provides visible light at the ablation points, allowing the physician the ability to view the relative position of where the laser energy from the ablative laser source will hit. The laser apparatus in FIG. 4 also includes an alignment laser 406, which is a low powered visible laser device, such as a laser diode in the visible spectrum at 630 nm, that provides a light beam into the fiber optic bundle by use of a dicroic splitter 407, a coated mirror, or similar device or means for providing more than one light beam to a single location. These devices can be manufactured with coatings that will reflect visible light and transmit near infrared light at 1064 nm, typically generated from a YAG laser.

For example, a mirror can be coated on one side so that it reflects light from one side and is transparent to light from the other side. The dicroic splitter 407 and alignment laser 406 can be positioned in such a way that the visible light beam will be co-linear with the ablative laser beam. Because the materials used in the fiber bundle device can pass both visible and near infrared laser energy, both lasers can utilize the same components without one affecting the other. FIG. 4 depicts the fiber optic bundle device (which includes a SMA connector 408 at the proximal end and a flexible protective jacket 403 at a distal end). The dicroic splitter 407 makes it possible for the alignment laser 406 to be on or off while therapy is being performed.

Figure 5:
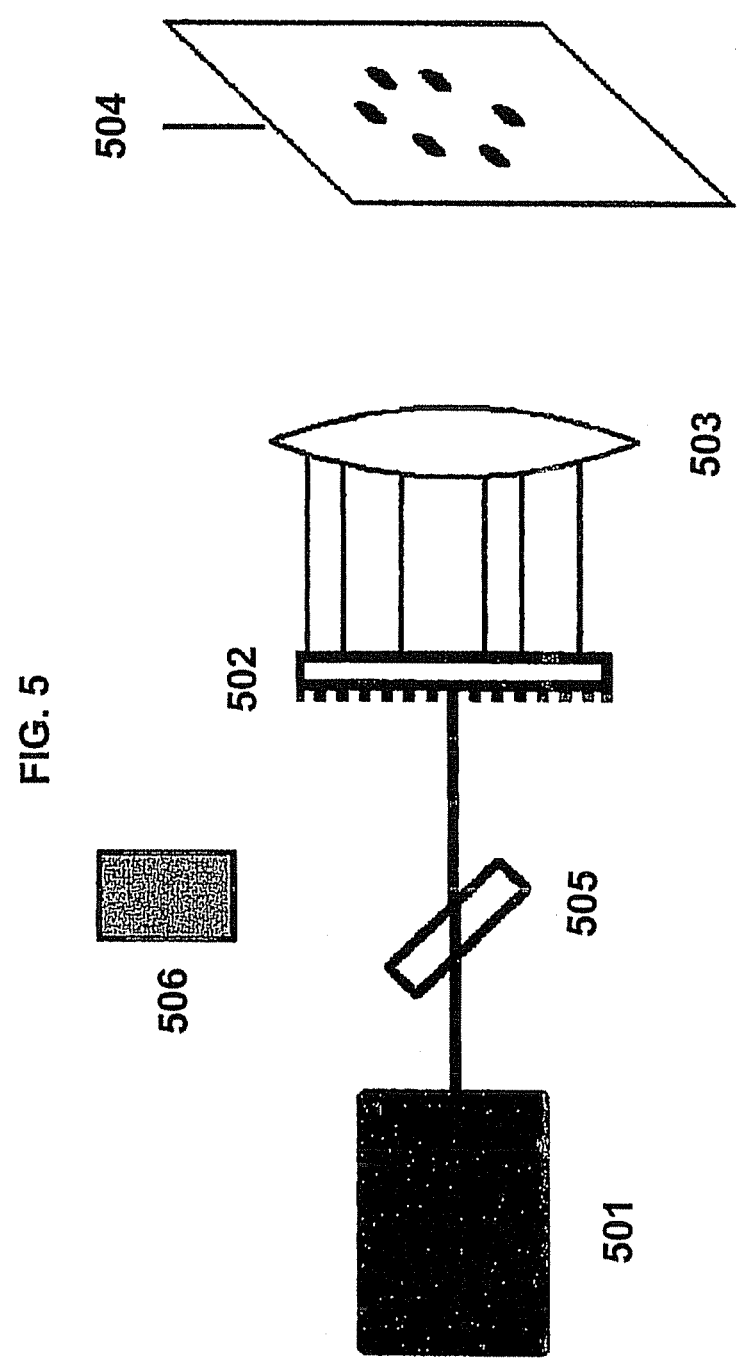
FIG. 5 shows a laser system using a diffractive optic for ablating a large number of epithelial cells in a desired location.
Figure 9:
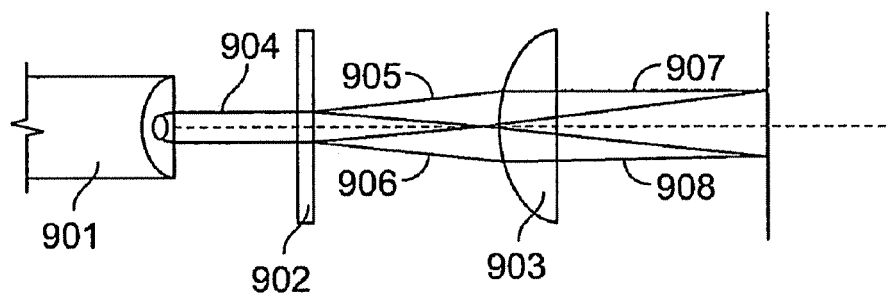
FIG. 9 shows how a focus lens can provide ablation points of a desired size or at a desired distance from laser light radiation provided by a diffractive optic.

FIG. 5 shows the use of a single optical element 502 such as a diffractive optic or binary optic to generate a plurality of laser beams. This optic alters phase relationship of the laser beam resulting in a distribution of the laser energy in a desired pattern. For example, a set of six focus spots are formed in a circular pattern at 3.75 mm for a primary focus lens 503 with a focus of 2 inches. Each diffractive optic 502 is designed with fixed characteristics, and the pattern of spots imaged by the primary focus lens 503 at the image plane 504 is fixed. FIG. 9 illustrates how a laser source 901 can interact with a diffractive optic 902 and a focus lens 903 downfield from the laser source 901. The laser source 901 provides laser beam 904 which passes through the diffractive optic 902 which can diffract the light to provide more than one laser beam. In FIG. 9, two laser beams 905 and 906 are provided by the diffractive optic 902, though a greater number of laser beams may be provided by other suitable diffractive optics. The focus lens 903 provides beams 907 and 908 whose diameters are narrowing and whose irradiance is increasing as they approach a focal point. As mentioned above, altering the location of the focus lens in relation to the focal length of the lens of the laser delivery system will increase or decrease the diameter, or separation, of the focus spots. The location of the focus lens 903 can be computer-controlled and/or motorized so that the distance from the optical fiber can be adjusted, thereby adjusting the separation between the ablation points. The motor actuation of the focus lens can be done by any means, such as electrical gear devices or piezoelectric activators.

Figure 6:
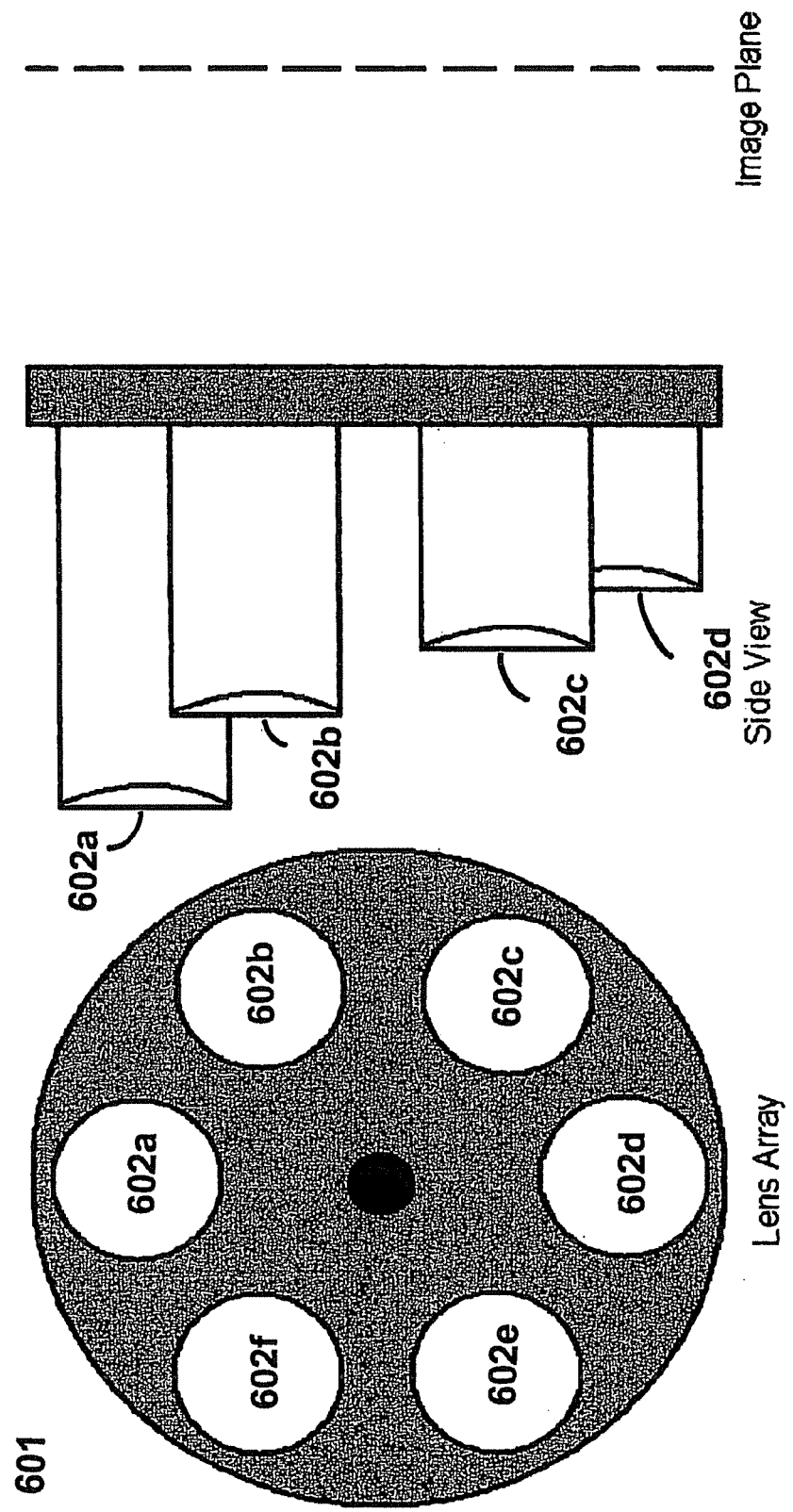
FIG. 6 shows a device for easily and precisely changing the laser spot pattern generated on a crystalline lens.

The diffractive optic or binary optic can be held in a rotation stage as illustrated for focus lenses in FIG. 6. Again, by rotating the optic, the six focus spots can be positioned at different positions along a fixed diameter.

FIG. 5 also shows the use of an alignment mechanism which provides visible light at the ablation points. An alignment beam 506 is provided as described in FIG. 4, although the diameter of the focus spot pattern may fall on a slightly different circumference because of the shorter wave length of the alignment laser. This can be compensated for by the addition of a negative correction lens in the alignment beam path before the dicroic splitter if it is determined that the differences in each circumference is significant to this application. FIG. 5 shows the optical system with a dicroic splitter 505 as described in connection with FIG. 4, though other devices or means may be used which provide more than one light beam to a single location. As discussed earlier, the dicroic splitter permits the alignment beam to remain in the on state during therapy with no adverse effects.

The fiber optic bundles and diffractive and binary optics described herein are exemplary of a broader class of optical components contemplated for generating a plurality of ablation points. For example, other elements such as beamsplitters, diffraction gratings, binary optics, diffractive optics, micro optics, filters, gratings, and others are contemplated. A preferred apparatus has an even number of laser beam-generating elements, for example an even number of optical fibers in a fiber optic bundle or an optic that produces an even number of focus spots. A laser-guiding element can be made to generate these spots that are equal distance around the circumference from each other to keep the desired symmetry.

It is also possible to produce spots that are offset from the center line. In previous examples, the laser beam was directed at the center and normal to the lens. In other words, the laser beam hits the lens at a 90 degree angle. This will produce a focus spot that is collinear, that is, on the same center line as the laser. A line could be drawn from the spot at best focus, through the center of the lens and back down the center of the laser beam all the way back to the laser. However, the laser can be adjusted off this centerline and then pointed back towards the focusing lens such that the beam still hits the center of the lens. A line drawn down the center of the beam to the lens and compared to the original centerline, will be an offset of a few degrees.

If the angle between the original centerline and the new beam path is offset by 10 degrees, the focusing lens will still produce a focus spot at the same distance from the lens. However, because the beam is entering the center of the lens at an angle, the focus spot now produced is also offset a few degrees. The lens tries to bend the laser beam back to the original centerline, but pointing the laser to the lens at an angle causes the focused spot to appear off to one side of the centerline. If a second laser is set up on the other side of the original centerline and pointed to the center of the lens, a second focus spot will be produced on the opposite side of the original centerline. The separation of the two focus spots are a combination of the total angle between the two beams, now 20 degrees, and the focal length of the lens. The longer the focal length of the lens, the greater the separation of the two spots at focus.

For the optical fiber bundles discussed above, if the fiber ends are tipped at an angle with respect to the focus lens (as shown in FIG. 8), the lens will produce separate spots as described above. However, if the fibers are not angled the lens can also be used to image the fiber tips which will also produce individual spots. The smallest focus spots that can be made are the diameters of the tips of the fibers for the non-angled fibers. This is referred to an image relay system. The diffractive optic works more like the example of the two lasers. A single beam is pointed to the center of the diffractive optic at 90 degrees of incidence. The diffractive optic causes 50% of the beam to steer off of the center line of the lens in one direction and 50% of the beam to steer off at the same angle but in the opposite direction. Just like in the example, the lens produces two focus spots because the two beams produced by the diffractive are coming at the lens at an angle. The separation of the two spots is a combination of the grating period of the diffractive optic and the focal length of the lens. For the diffractive system, if the diffractive remains constant, changing the focal length of the lens changes the spot separation.

A diffractive optic can be made to produce two spots when used with a focusing lens. The lens has a focal length of 50 mm. The separation of the two spots produced is 10 mm apart. Increasing the focal length of the lens will increase the separation of the two spots as described in the example of the two lasers pointing at a common lens. The longer the focal length of the lens, the greater the separation of the two focus spots. By increasing or decreasing the focal length of the lens in the diffractive system described, the separation can be adjusted for each individual patient. The diffractive is rotationally sensitive, that is, the two beams it produces rotate about a central axis as the diffractive is rotated. This allows for positioning the two spots at any angle on a fixed circumference. Again, changing the focus lens to a lens having a different focal length would allow for positioning the two spots on different circumferences to meet the needs of different patients.

Other techniques may be used to create a pattern of ablation points on the crystalline lens. For example, a mask can be used with a scanning mechanism or a laser beam having a wider diameter to created a desired pattern, as described in U.S. Pat. No. 6,263,879. A mask can be used to limit the laser beam to a defined pattern, thereby creating a desired ablation pattern, as described in U.S. Pat. Nos. 5,711,762 and 5,735,843. For example, a mask having slits with a circular or crescent shape may be used.

FIG. 6 shows a lens array for the laser delivery system which can be used to easily and precisely change the primary focus lens in the path of the laser light. The lens array comprises a housing 601 having openings for a plurality of focus lens. The housing 601 shown in FIG. 6 has six openings for focus lenses 602a through 602f. In the lens array, each circle 602a, 602b, 602c, 602d, 602e, and 602f, represents a single focus lens (such as those represented as focus lens 404 in FIG. 4 and focus lens 503 in FIG. 5). As shown in the side view of FIG. 6, the lenses 602a, 602b, 602c, and 602d may be held out from the housing 601 (in the side view, lens 602e and 602f are hidden by lenses 602b and 602c). FIG. 6 shows the lens 602a through 602d held out at different distances, however, it is preferable that the lenses be held at the same distance from the housing or within the housing itself. The lens array is located after the fiber optic bundle or the diffractive optic. The lens array is rotatable such that all the laser light beam illuminates only one lens of the lens array. The lens array can be used to alter the circumference of the focus spot pattern. The side view of this device shows how different focal length lenses can be offset in simple holders so that the image plane remains constant by fixing each lens at different distances to the image plane to compensate for the different focal lengths of these primary focus lenses. The focal lengths may vary, for example, by 0.01 to 2 millimeters.

The laser delivery system can also include a mechanism for sliding the focus lens closer to or farther from the patient. The focus lens could be adjusted by a sliding means, such as where a lens would be disposed on a sliding adjustment stage that would move in the longitudinal direction, either closer to or farther from the eye to be treated. The lens would be disposed on a slide having a micrometer-scale adjustment capacity. For example, the distance of the lens from the eye to be treated could be adjusted from an initial focal length of 50 millimeters to an adjusted focal length of 51 millimeters.

The laser delivery system can also include a mechanism to rotate the laser beams so that an additional set of ablations can be made on a single patient. Means for rotating the laser beams include automated and manual devices and include wheels or turntables in which the laser element is in the middle or the circumference. Such mechanisms for rotation facilitate making ablations to the crystalline lens in more than one step. For example, if 1,000 ablation points on the crystalline lens are to be made, the practitioner may wish to make 500 at one time, followed by 500 at a second time. It may be desirable to have a smaller number of laser beam-generating elements connected to a single laser source in order to avoid excessive power requirements for the laser source. For this option, it may be desirable to dispose a plurality of laser spot-generating elements on a wheel that can be rotated. Preferably, the wheel can be accurately and precisely rotated, for example, with precision on a micrometer scale. The doctor or other medical practitioner who is performing the procedure could then locate that wheel at a second position for a crystalline lens, and then by just using a micrometer on this slide, make a one millimeter adjustment for this stage. The patient would remain in the same location.

Figure 7:
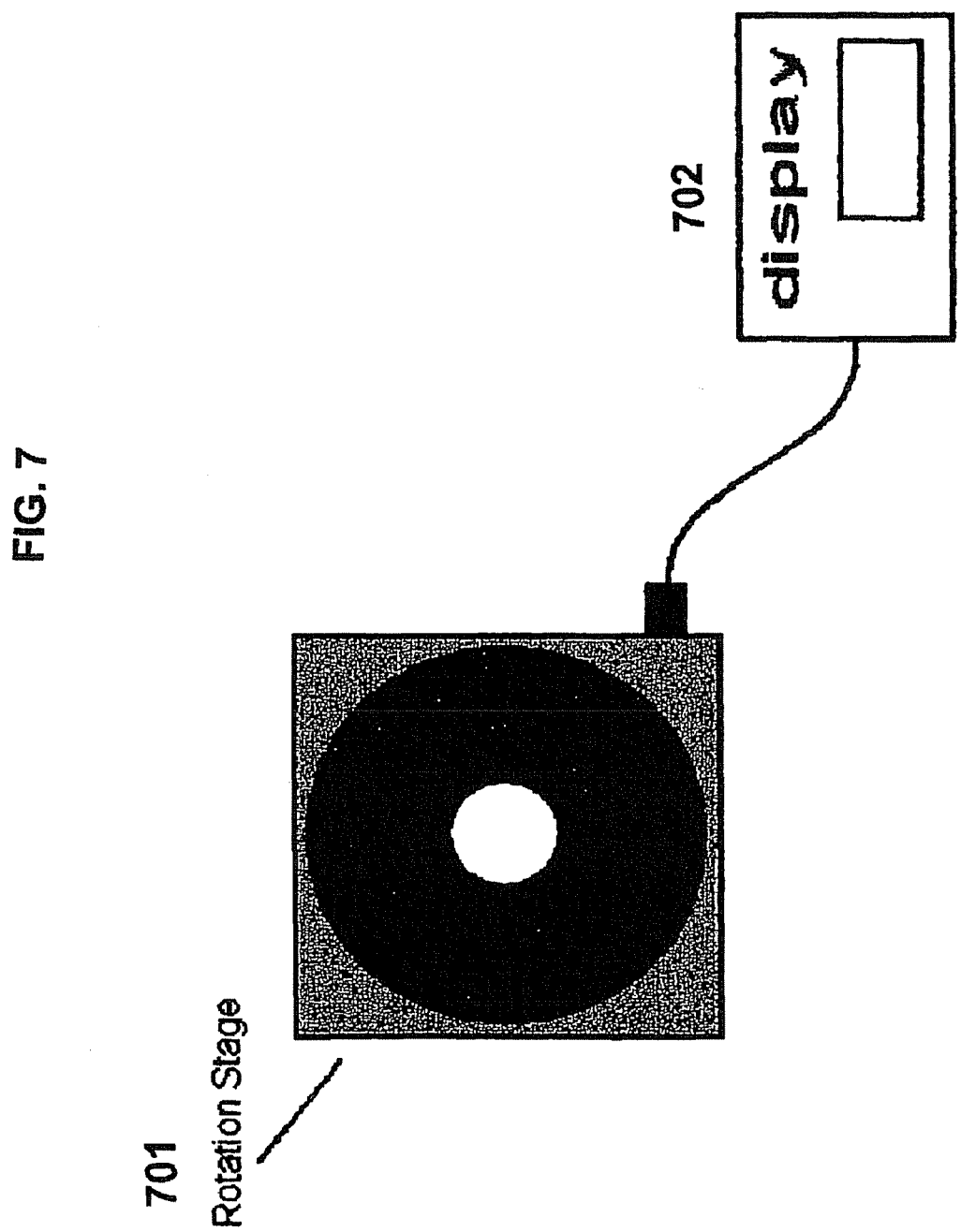
FIG. 7 shows a mechanical rotation stage for precisely rotating the ablation points by small amounts.

FIG. 7 shows a mechanical rotation stage for precisely rotating the ablation points. The center of the device is hollow so that fixtures for the fiber optic bundle, diffractive optic or binary optic can be affixed in such a way that the device can be rotated with a minimal amount of off-axis steering. Off-axis steering can cause the spots to rotate out of position at the target area. It is worth noting that because the laser beam passes through the diffractive optic or binary optic, it is generally unaffected by off-axis steering, whereas this problem greater consideration for the fiber optic bundle array.

The apparatus may further comprise a digital display that is operatively connected to a rotation wheel equipped with an encoder or other feedback mechanism so that the position of the laser spot-generating element (the optic) can be set to a precise degree. The digital display can indicate where the laser spots will be generated to a significant degree of accuracy, for example to one-hundredth of a degree. Using such a digital display, the laser spot-generating element can be rotated, for example from zero to 359.99. This provides precise feedback as to where the laser spot-generating elements are in rotation around that circumference, so one could always keep track. Alternatively, the rotation of the laser spot-generating elements can be motorized. A small motor could be placed on a rotation wheel with the feedback and the doctor can either drive it to that next position or enter the desired degrees of rotation and the laser spot-generating element will rotate to the entered position.

For example, it may be desirable to make 64 ablation points. One option is to have 64 laser spot-generating elements associated with a single laser source. There would just be one fire of a laser and the treatment is done. However, the consequence is that the power of the laser source is divided into 64 parts. If the laser does not have sufficient power to provide enough energy for each of those 64 spots, then the procedure will not be as effective as desirable. One solution is to provide a larger laser, since the power of the laser is limiting how many spots can be generated. Another solution is to divide the laser into a lesser number of laser spot-generating elements, and apply the laser spots to the crystalline lens in more than one step, as described herein.

An option for adjusting the spacing of ablation points comprises substituting a focus lens having a different focal length. The operator can make a slight adjustment. Those slides can also be motorized and it can also have feedback with a digital display providing high precision. A high degree of accuracy can be provided with linear or rotational stages having encoders built into them.

A translation stage in an operational system can be used to customize the spot diameter for different size eyes of different patients. With an array of lenses in place, the right lens position can be selected and then an adjustment can be made to offset the focus so that the subject remains at the same place. Offsets for a focal length change of the lens are relatively small, typically on the order of only a few millimeters for the methods described here.

There is substantial imagery laying, magnifications, and optics in between the optical fibers, the tips of the optical fibers, and the location of the subject. Relaying the image of the ends of the fibers and magnification has to be taken into account. If the magnification is changed, for example from of 1:1 to 1:8, the ablation points will be further apart. The result is to effectively de-magnified, or make a larger spot array in the image plane. One of ordinary skill will recognize that the size of the circular spot made by the array of fibers on the far end or the output end will be changed by changing the magnification of the optical system between the subject and the ends of the fiber.

Another way is to take two or more optical fibers and manipulate them independently of each other such that the light being emitted to a lens hits the lens on a slight angle and if each of those are on slightly different angles, the lens will image two spots, effectively the same diameters, and that separation is a function of how much the angle of the fiber is tipped as it shines onto the lens. It is contemplated that a single optical fiber split into two may be used, which is commercially available equipment. This would require very precisely positioning those angles such that if a line were drawn directly through the center of the eye, if one optical fiber is rotated 3 degrees so that it hits the lens on a 3 degree angle, instead of straight down the middle, and rotate the other fiber is rotated 3 degrees, it is necessary to ensure that both of those optical fibers are very precisely 3 degrees of angle towards the lens. If one of those angles is 3 degrees and one of is different, for example 2.8 degrees, one spot is going to be drawing a different arc than the other, the result will be essentially two different circumferences being ablated. The undesirable result would be asymmetric pattern of ablation points but rather a pattern that is egg-shaped or oval. There are other processes for generating multiple spots using tips of optical fibers, for example, by manipulating their magnification in an array or bundle or using individual optical fibers and manipulating them individually and changing their angles with an impingement angle to the lens.

Other techniques for making a plurality of ablation points are also contemplated. For example, a laser apparatus having a scanning feature may be used. The scanning feature moves the laser beam so that the ablation point is moved. Scanning laser apparatus are known in the art and are used to generated lines by moving the laser beam back and forth. Ablation spots can be made by moving the laser beam in a scanning motion, preferably under computer control to create a desired pattern of ablation. For example, a computer controlled scanning mirror can move or scan a laser beam in the X-Y direction at the focal plane. The scanning can be carried out in a variety of patterns. For example, dots, circles, or curved lines may be created. Additional description and illustration of scanning laser techniques can be found in U.S. Pat. Nos. 6,325,792 and 6,706,036 (which are incorporated by reference herein), though ablation of the cornea is illustrated in those patents rather than ablation of epithelial cells of the crystalline lens.

Optionally, a biochemical approach may be used alternatively to or additionally with the laser-based approach, where one or more biochemically active agents are used to inhibit epithelial cell mitosis. Suitable biochemically active agents may include Taxol, Nocodazole or other spindle inhibitors, or Hydroxyurea or other nucleotide synthesis inhibitors. A suitable biochemically active agent may be in admixture with an organic or inorganic carrier or excipient suitable for administration to the eye. Alternatively, the biochemically active agent may be ingested or injected. Preferably, the active chemical agent is administered through eye drops or an eye salve.

For example, the laser-based approach may be used to prepare cells, and thereafter eye drops containing a suitable biochemically active agent may be employed. Alternatively, a light-activated drug may be used.

All patents, test procedures, and other documents cited herein are fully incorporated by reference to the extent such disclosure is not inconsistent with this invention and for all jurisdictions in which such incorporation is permitted.

While the present invention has been described and illustrated by reference to particular embodiments, it will be appreciated by those of ordinary skill in the art that the invention lends itself to many different variations not illustrated herein. For these reasons, then, reference should be made solely to the appended claims for purposes of determining the true scope of the present invention.

Although the appendant claims have single appendices in accordance with U.S. patent practice, each of the features in any of the appendant claims can be combined with each of the features of other appendant claims or the main claim.

We claim:

1. An apparatus for ablating epithelial cells in a crystalline lens, the apparatus comprising:
    a laser source providing laser light radiation, wherein the laser source generates short pulses of laser light having a wavelength which will not damage a cornea;
    a laser delivery system operatively connected to the laser source for receiving the radiation from the laser source and generating a plurality of laser beams simultaneously that creates a pattern of ablation points on the crystalline lens, wherein the pattern comprises separate spots; and
    a computer controller which is operatively connected to the laser delivery system to control delivery of the laser beams to the epithelial cells.

2. The apparatus of claim 1, wherein the laser provides radiation having a wavelength in the range of about 400 nm to about 1400 nm.

3. The apparatus of claim 1, wherein the laser delivery system comprises a fiber optic bundle.

4. The apparatus of claim 3, wherein the fiber optic bundle is held in a stage that can rotate the bundle.

5. The apparatus of claim 1, wherein the laser delivery system comprises a diffractive optic or a binary optic.

6. The apparatus of claim 1, wherein the laser delivery system comprises a focus lens for receiving and focusing the plurality of laser beams, wherein the focus lens is located after a fiber optic bundle, a diffractive optic or a binary optic.

7. The apparatus of claim 6, wherein the laser delivery system comprises a plurality of focus lenses having different focal lengths.

8. The apparatus of claim 1, wherein the laser delivery system comprises a rotator for automatically rotating the plurality of laser beams.

9. The apparatus of claim 1, wherein the laser apparatus comprises an alignment mechanism which provides visible light at the ablation points.

10. The apparatus of claim 1, wherein the laser provides radiation having a wavelength of about 1064 nm.

11. The apparatus of claim 1, wherein the laser provides radiation having a wavelength from about 400 nm to about 1064 nm.

12. The apparatus of claim 1, wherein the laser provides radiation having a wavelength from about 400 nm to about 700 nm.

13. The apparatus of claim 1, wherein the plurality of laser beams produces an even number of separate spots.

14. The apparatus of claim 1, wherein the plurality of laser beams produces 6 or more separate spots.

15. The apparatus of claim 14, wherein the separate spots are formed in a circular pattern.

16. The apparatus of claim 1, wherein the plurality of laser beams produces from 8 to 120 separate spots.

17. The apparatus of claim 1, further comprising an apparatus for measuring thickness of a cornea, and adjusting the laser delivery system based upon the measured thickness.

18. An apparatus for ablating epithelial cells in a crystalline lens, the apparatus comprising:
    a laser source providing laser light radiation, wherein the laser source generates short pulses of laser light having a wavelength which will not damage a cornea;
    a laser delivery system operatively connected to the laser source for receiving the radiation from the laser source and generating a plurality of laser beams that creates a pattern of ablation points on the crystalline lens, wherein the pattern comprises separate spots,
    wherein the laser delivery system comprises a diffractive optic or a binary optic, and
    wherein the diffractive optic or binary optic is held in a stage that can rotate the diffractive optic or binary optic.

19. An apparatus for ablating epithelial cells in a crystalline lens, the apparatus comprising:
    a YAG laser source providing laser light radiation having a pulse length of about 1 picosecond or less;
    a laser delivery system operatively connected to the laser source for receiving the radiation from the laser source and generating a plurality of laser beams simultaneously that provide a pattern of separate spots, wherein the laser delivery system further comprises a rotator adapted for rotating the separate spots provided by the laser beams, and
    a computer controller which is operatively connected to the laser delivery system to control delivery of the laser beams to the epithelial cells.

* * * * *